(12) United States Patent
Musho et al.

(10) Patent No.: US 8,529,742 B2
(45) Date of Patent: Sep. 10, 2013

(54) ELECTROCHEMICAL SENSOR WITH CONTROLLED VARIATION OF WORKING ELECTRODE

(76) Inventors: Matthew K. Musho, York, PA (US); Nicholas F. Szabo, York, PA (US)

(*) Notice: Subject to any disclaimer, the term of this patent is extended or adjusted under 35 U.S.C. 154(b) by 671 days.

(21) Appl. No.: 12/711,806

(22) Filed: Feb. 24, 2010

(65) Prior Publication Data
US 2011/0203926 A1 Aug. 25, 2011

(51) Int. Cl.
*G01N 27/327* (2006.01)

(52) U.S. Cl.
USPC ............................. 204/412; 422/68.1

(58) Field of Classification Search
USPC .............. 204/400, 403.01–403.15, 412, 434, 204/290.01; 422/68.1, 82.01–82.03, 98; 435/5
See application file for complete search history.

(56) References Cited

U.S. PATENT DOCUMENTS

| 4,081,653 A | 3/1978 | Koo et al. |
|---|---|---|
| 6,662,439 B1 | 12/2003 | Bhullar |
| 7,294,246 B2 | 11/2007 | Gundel et al. |
| 2003/0003524 A1* | 1/2003 | Taniike et al. ............ 435/25 |
| 2007/0227911 A1 | 10/2007 | Wang et al. |
| 2008/0011616 A1* | 1/2008 | Brown ................. 205/777.5 |

FOREIGN PATENT DOCUMENTS

| EP | 1195441 A1 | 10/2002 |
|---|---|---|
| EP | 1431758 A1 | 6/2004 |
| EP | 1541998 A1 | 6/2005 |
| JP | 05-072172 A | 6/1989 |
| WO | 9913099 | 3/1999 |

* cited by examiner

*Primary Examiner* — J. Christopher Ball
(74) *Attorney, Agent, or Firm* — McNees, Wallace & Nurick, LLC

(57) ABSTRACT

An electrochemical sensor includes a dielectric substrate and a conductive layer formed on a surface of the substrate. The conductive layer includes a working electrode, an electrode lead and a connecting arm connecting the working electrode to the electrode lead. A dielectric layer is positioned over the conductive layer. The dielectric layer has an aperture exposing the working electrode and a portion of the connecting arm. The working electrode, electrode lead and connecting arm may be formed by laser ablation technique to provide precise working electrode sensor parameters.

18 Claims, 3 Drawing Sheets

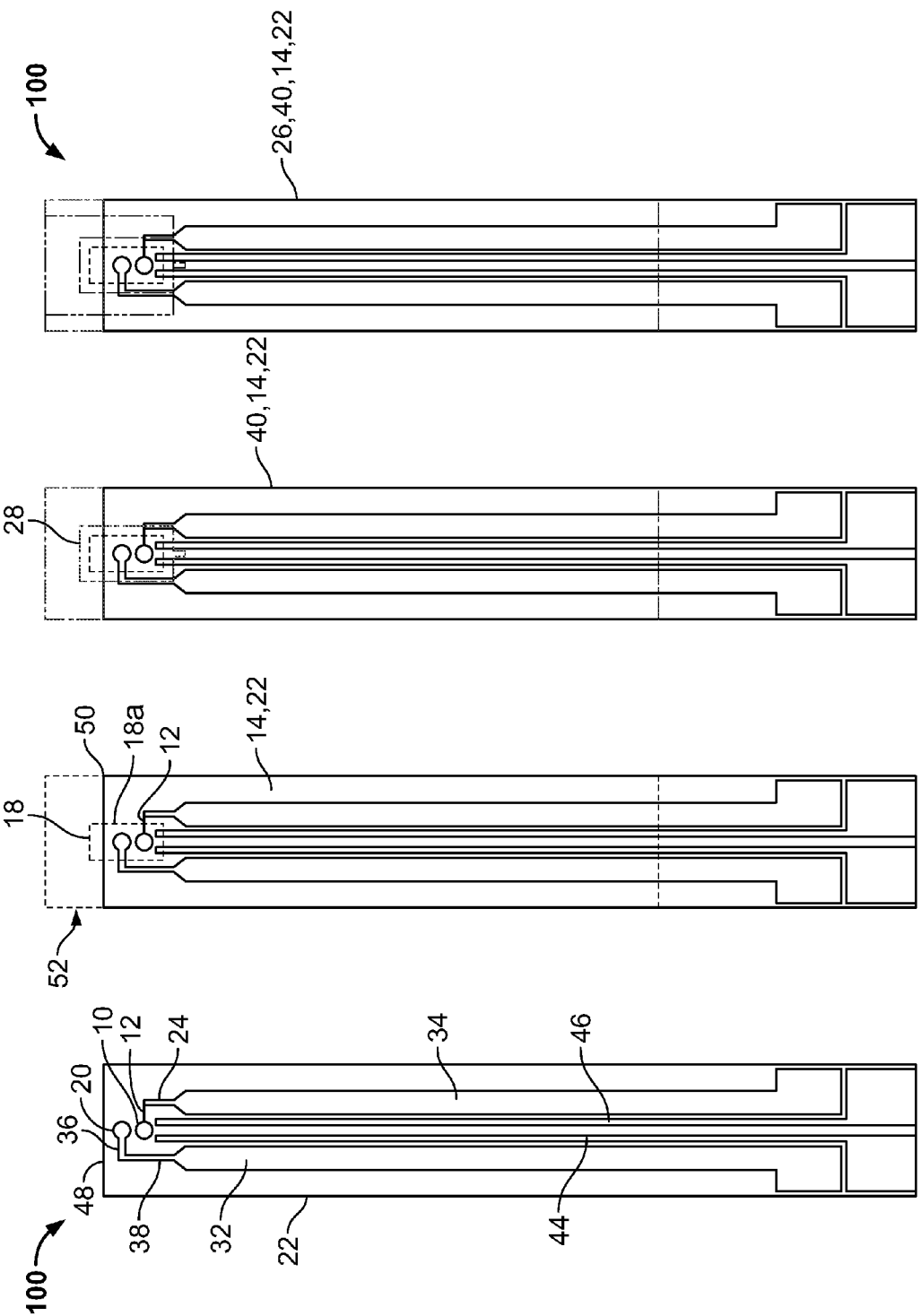

ELECTROCHEMICAL SENSOR WITH CONTROLLED VARIATION OF WORKING ELECTRODE

FIELD OF THE INVENTION

The present invention is directed to an electrochemical sensor, and more particularly to an electrochemical sensor with controlled variation of a working electrode where the electrochemical response is dependent on the size of the working electrode.

BACKGROUND OF THE INVENTION

A typical disposable electrochemical sensor for blood glucose monitoring includes a substrate film upon which a layer of conductive material is deposited and patterned to form electrodes. Traditionally electrochemical cells, or biosensors, are comprised of three electrodes, a working electrode or sensing electrode, a reference electrode, and a counter electrode or auxiliary electrode. The working electrode is where the reaction of interest occurs at a fixed applied potential versus the reference electrode. The reference electrode functions to maintain a stable electrical potential on the working electrode. The counter electrode allows current to flow between the working electrode and the counter electrode so as not to disturb the reference electrode function. In cases when the system potential is inherently stable or small fluctuations in potential are not a concern, the reference and counter electrodes can be combined into a single reference/counter electrode paired with a working electrode. In some instances electrochemical biosensors use amperometry to quantify specific analyte concentration(s). The working electrode, provides a response proportional to its exposed surface area. During fabrication, the manufacture closely controls the process variation associated with the working electrode area.

Normally the working electrode is formed from two or more elements. One element is a conductive layer that forms the active element facilitating electron transfer to or from an electro-active species which are generated when the sample is applied to the sensor. A second element is a dielectric layer that defines, along with the first element, the actual dimensions of the working electrode that is in contact with the sample fluid. The second element forms a window over a portion of the conductive layer. Variation in either element may result in a variation in the sensor response. The second element or dielectric layer may therefore directly influence the accuracy of the reading.

Some prior art sensors reduce the effects of inaccurately applying the dielectric layer on the final electrode surface area by using a plurality of conductive neck sections in a symmetrical pattern. The window in the dielectric layer may shift slightly, because symmetrically arranged neck sections compensate for the shift. In such sensors, the dielectric layer may be poorly defined but the effect of the poor definition may be minimized because the neck intersecting the dielectric layer edge is very small. However, such sensors require very precise definition of a number of all conductive neck sections, for example, two different neck sections, on a typical sensor. Some of these precisely defined conductive neck sections are not even connected to an external circuit, although it is still necessary to precisely define the neck sections for symmetry, which increases the complexity and costs of fabricating the sensor.

In prior art electrodes the surface areas may be defined by either conductive layer patterning or dielectric layer patterning and registration. There is a need for a means of more accurately defining the sensor's working electrode to simplify the process of forming an accurate biosensor.

SUMMARY OF THE INVENTION

In one embodiment, an electrochemical sensor includes a dielectric substrate and a conductive layer formed on a surface of the substrate. The conductive layer includes a working electrode, an electrode lead and a connecting arm connecting the working electrode to the electrode lead. A dielectric layer is positioned over the conductive layer. The dielectric layer has an aperture exposing the working electrode and a portion of the connecting arm.

One advantage is that the size of electrodes may be decreased and the accuracy of the defined electrode surface area is not significantly modified compared to prior art electrodes.

Another advantage is the ability to limit the effect of the dielectric layer patterning on electrode area and size accuracy. This enables the biosensor dielectric layer to be patterned using existing low cost, less accurate methods while at the same time preserving electrode accuracy.

Another advantage of the method is to provide an even more accurate electrode with an improved dielectric layer patterning process. Both of these provide improvements to the manufacture and use of the electrochemical sensor.

Still another advantage is the ability to define accurately the electrode surface area. Accuracy of the sensor can thus be more directly related to the accuracy of the conductive layer definition than that of the dielectric layer definition. Small electrodes with desired area coefficients of variation (COVs), which is equal to the ratio of the area standard deviation to the area mean, may be made with less precise electrode patterning methods, e.g., screen printing and lamination. The electrode area COV for the present invention may approach that of the conductive layer patterning process.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIG. 4 illustrates a plan view of an exemplary gold (Au) ablated film or substrate layer.

FIG. 5 illustrates a plan view of an exemplary dielectric layer.

FIG. 6 illustrates a plan view of an exemplary spacer layer.

FIG. 7 illustrates a plan view of an exemplary cover or lid.

DETAILED DESCRIPTION OF THE INVENTION

The present invention discloses an electrochemical sensor that is designed such that variations in a working electrode size come primarily from variations in an active element. Normal variations in other elements which are included in the sensor, for example, a printed or laminated isolation layer, do not affect the size of the working electrode, and therefore there is no variation in the response generated by the working electrode due to other elements. Elimination of variations in the working electrode is accomplished by minimizing a connecting feature between the working electrode and an electrical connector or lead.

The working electrode and other conductive features, for example, an element connecting the working electrode to a lead, may be formed using laser ablation, a process which can produce elements with features that are less than one-thousandth of an inch. Laser ablation enables the precise definition of such electrical connecting leads, working electrodes and other features, which is required to reduce coefficient of variation and provide accurate measurements. Metalized films may be imaged using laser ablation, such as Au, Pd, and Pt or any metal having similar electrochemical properties that can be sputtered or coated on plastic substrates such as PET or polycarbonate, or other dielectric material. The primary sensor features may be created by laser-ablating a thin metal film carried on a polymer substrate.

Figure 1:
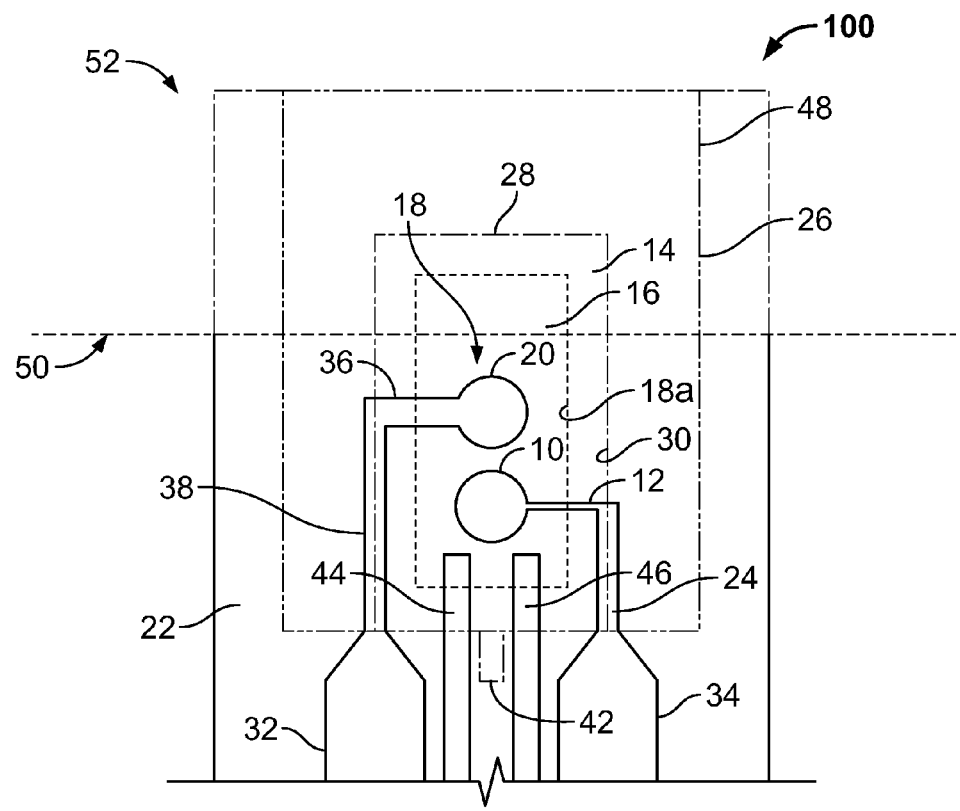
FIG. 1 illustrates a partial plan view of one embodiment of an electrochemical sensor.

Referring to FIG. 1, a sensor 100 includes a working electrode 10 that is connected by a connecting arm 12 to a lead trace 24. In at least one embodiment connecting arm 12 may be as narrow as 10 microns. In alternate embodiments connecting arm 12 may be 20 microns wide, or have a width that contributes so little to the sensor response that variations in its definition by itself or by the dielectric opening produce negligible effects on the sensor response. The lead trace 24 is an extension of lead 34 and electrically connects connecting arm 12 with lead 34. A reference or counter electrode 20 is disposed adjacent to working electrode 10 on a polymer substrate 22, e.g., polycarbonate or polyethylene terephthalate (PET). Reference/counter electrode 20 is electrically connected to a lead 32 by connecting arm 36 and lead trace 38. A dielectric layer 14 may be laminated or printed over substrate 22. Dielectric layer 22 includes an aperture 16 which defines an area or window 18 of electrodes 10, 20 that is exposed to the test fluids. In at least one embodiment, the exposed areas from the working electrode 10 may have a circular area of approximately 0.320 mm² and its connecting arm of finite, but small width or about 1.2% of the total area of working electrode 10 constitutes the reactive area. In at least one exemplary embodiment, dielectric layer 14 can move ±0.250 mm with respect to the point at which window line 18a crosses connecting arm 24. The variation in the working electrode area associated with a movement of ±0.250 mm results in a variation in the total working electrode area of about 0.003 mm², or about 1% of the total working electrode area. A vent 42 is disposed on sensor 100 between a pair of fill detect electrodes 44, 46. Vent 42 is in fluid communication with a capillary channel 30 and allows air to escape from capillary channel 30 when fluid enters the capillary channel 30. Fill detect electrodes 44, 46 detect the presence of fluid in capillary channel 30.

Figure 2:
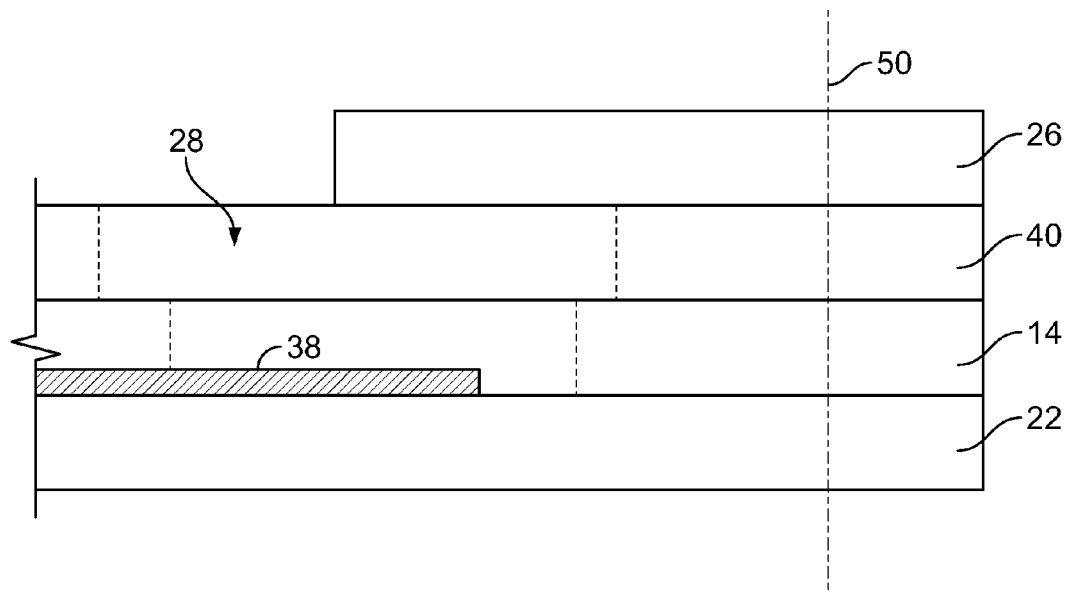
FIG. 2 illustrates a cross-sectional elevational view of the electrochemical sensor of FIG. 1.

Referring next to FIG. 2, a cross-sectional view of sensor 100 shows the arrangement of laminations. In addition to substrate 22 and dielectric layer 14, capillary lid 26 and a spacer layer 40 are laminated together to form sensor 100. Spacer layer 40 includes an aperture 28 that defines capillary channel 30 for receiving fluid. In alternate embodiments the dielectric layer may be screen-printed, photolithographically patterned, or laminated over the conductive layer.

Figure 3:
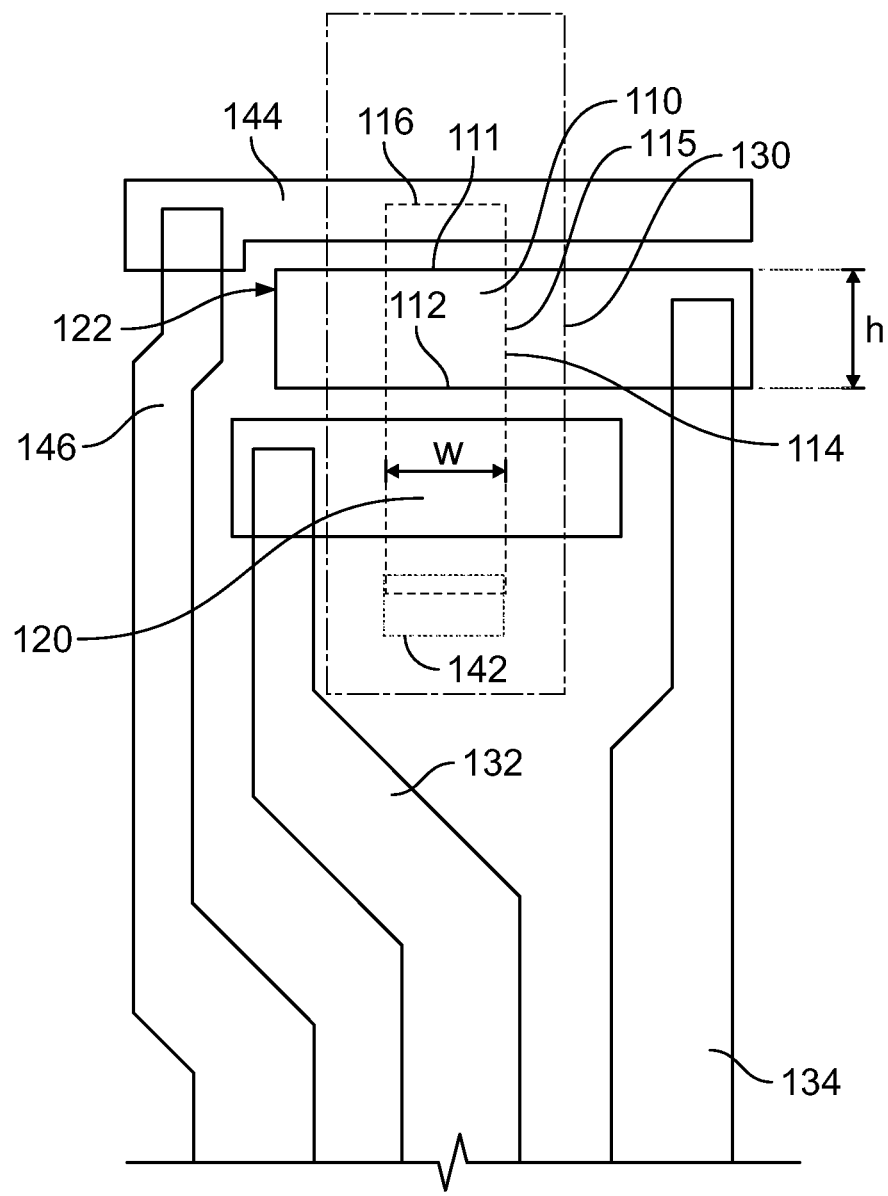
FIG. 3 illustrates a partial plan view of an alternate embodiment of an electrochemical sensor.

Referring next to FIG. 3, another exemplary method for controlling the working electrode size involves definition of working electrode 110 by one or more features. In FIG. 3, a working electrode 110 is defined by an opening in a dielectric layer 114. Dielectric layer 114 is disposed over a conductive carbon layer 122 in such a manner so that opposing edges 115, 116 of dielectric layer, along with the opposing edges 111, 112 of carbon layer 122 and working electrode 110 that intersect edges 115, 116 of dielectric layer 114 define area h×w of working electrode 110. Reference/counter electrode 120 is also similarly defined by dielectric layer 114, and has exposed dimensions h, w that are substantially the same as of working electrode 110. A vent hole 142 is provided at one end of capillary channel 130. Vent hole 142 provides fluid communication between capillary channel 130 and the exterior air to allow fluid to displace air in capillary channel 130. Fill detector electrode 144 is partially exposed in capillary channel 130, and connects to fill electrode contact 146. Contact 132 and 134 provide electrical communication with reference electrode 120 and working electrode 110, respectively.

The variation in the working electrode's area is related to the variation in the dielectric opening. In the exemplary embodiment shown in FIG. 1, where the dielectric layer 18 intersects the connecting arm 12, the area of working electrode 10 may be 0.320 mm² and the area of connecting arm 18 may be 0.004 mm², which are exposed to the test fluid. The response of sensor 100 is directly proportional to these exposed areas. The expected variation in dielectric layer window 18 position as it traverses the connecting arm 12 is ±0.025 mm. The expected variation corresponding to the exposed area when the connecting arm 12 is 13 microns wide is 0.003 mm² or ~1%.

In FIG. 3, working electrode 110 may be defined by two dimensional parameters in layers 122, 114. One parameter is the conductive portion of the working electrode's 110 vertical dimension h on substrate layer 122 and the other parameter w is the width of the dielectric layer 114. In an exemplary embodiment the area of working electrode 110 may be defined by a length (h) of 0.635 mm and a width (w) of 0.508 mm). The expected variation in each dimension may be about ±0.025 mm. The resultant variation in the working electrode's area is defined by Equation 2:

$$\Delta w/w + \Delta h/h = 9\%$$

Referring next to FIG. 4, an exemplary ablated film layer or substrate 22 includes ablated gold contacts 10, 20. End 48 corresponds with a die cut line 50 (FIG. 5). Also shown in FIG. 4 are the full-length electrode leads 32, 34, 44, 46, lead traces 24, 38 and connecting arms 12, 36. FIG. 5 shows dielectric layer 14 overlaying substrate 22. Die cut line 50 indicates the location where the top portion 52 is detached from the final sensor 100. Aperture 18 in dielectric layer 14 defines window 18 with line 18a crossing over connecting arm 12. FIG. 6 shows spacer layer 40 that is applied over dielectric layer 14 so that aperture 28 exposes dielectric opening 18 and the components, e.g., working electrode 10 and reference electrode 20, and connecting arms 12, 36 within the working area defined by dielectric window 18. Finally, FIG. 7 shows capillary lid 26 applied over top of spacer layer 40. Capillary lid 26 seals the capillary channel 30 so that the volume of test fluid is limited and fluid may only enter capillary channel at end 48.

FIGS. 4-7 show an assembly sequence which, for illustration purposes represents each of laminated layers 14, 22, 26 and 40 as transparent layers, in order that the relationship of functional elements can be appreciated. It should be understood that in practice, any of the laminated layers 14, 22, 26 and 40 may be opaque or translucent, such that underlying layers and associated elements may not be visible in the finished sensor 100.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An electrochemical sensor comprising:
    a dielectric substrate;
    a conductive layer formed on a surface of the substrate, the conductive layer comprising at least one working electrode, an electrode lead and a connecting arm connecting the working electrode to the electrode lead; and
    a dielectric layer disposed over at least a portion of the conductive layer, the dielectric layer including an aperture exposing the working electrode and at least a portion of the connecting arm;
    wherein at least one of the width or length of the connecting arm does not exceed 0.0254 mm.

2. The sensor of claim 1, wherein a variation in the working electrode area associated with a movement of ±0.250 mm of the dielectric layer results in a variation in a total working electrode area of about 0.003 mm$^2$, the variation in the total working electrode area equaling about 1% of the total working electrode area.

3. The sensor of claim 1, wherein the working electrode, the connecting arm and the electrode lead are formed using laser ablation.

4. The sensor of claim 1, wherein the working electrode, the connecting arm and the electrode lead are formed using a process that can produce elements with features that are less than 0.0254 mm.

5. The sensor of claim 1, the working electrode, connecting arm and electrode lead comprising metalized films, the metalized films being imaged using laser ablation.

6. The sensor of claim 5, wherein the metalized films are selected from the group consisting of Au, Pd, Pt or any metal that is interest in an electrochemical sense which can be sputtered or coated.

7. The sensor of claim 6, wherein the substrate is selected from the group consisting of PET, polycarbonate, and other plastic materials.

8. The sensor of claim 1, wherein the working electrode, the electrode lead and the connecting arm are formed by laser-ablating a thin metal film carried on the substrate.

9. The sensor of claim 1 wherein the connecting arm is less than 0.02 mm.

10. The sensor of claim 1, further comprising a reference/counter electrode disposed adjacent to the working electrode, the reference/counter electrode electrically connected to an electrode lead by a second connecting arm.

11. The sensor of claim 1, wherein the aperture defines an area of working electrode that is exposed to a test fluid.

12. The sensor of claim 1, wherein the working electrode further comprises a circular area of approximately 0.320 square millimeters, the circular area being approximately equal to about 1.2% of the total area of the working electrode.

13. The sensor of claim 1 wherein a variation in the working electrode area associated with a movement of ±0.250 mm of the dielectric layer aperture results in a variation in the total working electrode area of about 0.003 mm$^2$, and the variation is about 1% of the total working electrode area.

14. The sensor of claim 1, further comprising a pair of fill detect electrodes with a vent disposed on the sensor between the fill detect electrodes, the vent arranged to allow air to escape from a capillary channel formed by a spacer layer and a cover lid portion, when a test fluid displaces air when entering the capillary channel.

15. The sensor of claim 14 wherein the fill detect electrodes detect the presence of fluid in the capillary channel.

16. The sensor of claim 1, further comprising a capillary lid applied over a spacer layer, the spacer layer applied over dielectric layer and further comprising an aperture defining a capillary channel for receiving a fluid.

17. The sensor of claim 1, wherein the dielectric layer is screen-printed, patterned, or laminated over the conductive layer.

18. The sensor of claim 1, wherein the electrode lead further comprises a lead trace extending from the lead to the connecting arm to form a electrically conductive path between the connecting arm and the electrode lead.

* * * * *